(12) United States Patent
Shevchencko et al.

(10) Patent No.: US 7,886,875 B2
(45) Date of Patent: Feb. 15, 2011

(54) SYSTEMS AND METHODS FOR MONITORING GAS TURBINE ENGINES

(75) Inventors: Eric A Shevchencko, Andover, CT (US);
Robert D Szolomayer, Glastonbury, CT (US)

(73) Assignee: United Technologies Corp., East Hartford, CT (US)

( * ) Notice: Subject to any disclaimer, the term of this patent is extended or adjusted under 35 U.S.C. 154(b) by 1158 days.

(21) Appl. No.: 11/776,176

(22) Filed: Jul. 11, 2007

(65) Prior Publication Data
US 2009/0014245 A1    Jan. 15, 2009

(51) Int. Cl.
*F01D 25/18*    (2006.01)
*G01L 7/00*    (2006.01)

(52) U.S. Cl. .................... 184/6.11; 184/6.4; 73/756
(58) Field of Classification Search .............. 184/6.4, 184/6.11; 73/756
See application file for complete search history.

(56) References Cited

U.S. PATENT DOCUMENTS

| | | | |
|---|---|---|---|
| 5,041,856 A | 8/1991 | Veronesi et al. | |
| 5,214,377 A | 5/1993 | Maurice et al. | |
| 5,264,832 A | 11/1993 | Parmer | |
| 5,610,341 A | 3/1997 | Tortora | |
| 5,760,298 A | 6/1998 | Fisher et al. | |
| 6,445,177 B1 | 9/2002 | Higgins | |
| 6,745,568 B1 * | 6/2004 | Squires | 60/605.3 |
| 6,776,261 B2 * | 8/2004 | Eriksen et al. | 184/6.4 |
| 7,009,198 B2 * | 3/2006 | Benfer et al. | 250/559.4 |
| 7,222,048 B2 | 5/2007 | Petchenev et al. | |
| 7,469,539 B2 * | 12/2008 | Squires | 60/605.3 |
| 2004/0237522 A1 * | 12/2004 | Squires | 60/605.3 |
| 2006/0047403 A1 | 3/2006 | Volponi et al. | |
| 2006/0081419 A1 | 4/2006 | Care et al. | |
| 2006/0248900 A1 | 11/2006 | Suciu et al. | |

* cited by examiner

Primary Examiner—Evan H Langdon

(57) ABSTRACT

Systems and methods for monitoring gas turbine engines are provided. In this regard, a representative method includes: monitoring lubrication oil at multiple locations of the gas turbine engine to detect a presence of debris in the oil; determining a characteristic of the debris in the oil; and correlating the characteristic of the debris with the location of detection to determine, while the gas turbine engine is operating, whether the engine is operating within predetermined limits.

11 Claims, 3 Drawing Sheets

SYSTEMS AND METHODS FOR MONITORING GAS TURBINE ENGINES

STATEMENT REGARDING FEDERALLY SPONSORED RESEARCH AND DEVELOPMENT

The U.S. Government may have an interest in the subject matter of this disclosure as provided for by the terms of contract number F33615-03-D-23540014 awarded by the United States Air Force.

BACKGROUND

1. Technical Field

The disclosure generally relates to gas turbine engine monitoring.

2. Description of the Related Art

Monitoring of lubrication oil of gas turbine engines for debris can be accomplished using a variety of techniques. By way of example, chemical analysis can be used to identify particles of deteriorating mechanical components. However, chemical analysis can be quite time-consuming and typically requires equipment that is used by ground maintenance personnel. Another technique involves the use of an oil filter that is removed from the engine so that captured debris can be analyzed. This technique also is typically performed by ground maintenance personnel.

Another technique involves debris capture devices, such as magnetic chip detectors. Unfortunately, magnetic chip detectors tend to be relatively inefficient at detecting debris.

SUMMARY

Systems and methods for monitoring gas turbine engines are provided. In this regard, a representative embodiment of a method comprises: monitoring lubrication oil at multiple locations of the gas turbine engine to detect a presence of debris in the oil; determining a characteristic of the debris in the oil; and correlating the characteristic of the debris with the location of detection to determine whether the engine is operating within predetermined limits while the gas turbine engine is operating.

Another embodiment of a method comprises: monitoring lubrication oil, at multiple locations of the gas turbine engine, to detect a presence of debris in the oil; approximating a source of origin of the debris; determining a characteristic of the debris; and correlating the characteristic with the source to determine whether the engine is operating within predetermined limits; the monitoring, approximating, determining and correlating being performed while the gas turbine engine is operating.

A representative embodiment of a system comprises: multiple debris capture devices operative to monitor lubrication oil of a gas turbine engine to detect a presence of debris in the oil; an oil debris monitor operative to monitor lubrication oil to determine a characteristic of the debris; and an oil analysis system operative to receive information corresponding to the presence of debris in the oil from the debris capture devices and information corresponding to the characteristic of the debris from the oil debris monitor; the oil analysis system being further operative to approximate a source of origin of the debris based on the information provided by the debris capture devices and correlate the characteristic with the source to determine whether the engine is operating within predetermined limits.

Other systems, methods, features and/or advantages of this disclosure will be or may become apparent to one with skill in the art upon examination of the following drawings and detailed description. It is intended that all such additional systems, methods, features and/or advantages be included within this description and be within the scope of the present disclosure.

BRIEF DESCRIPTION OF THE DRAWINGS

Many aspects of the disclosure can be better understood with reference to the following drawings. The components in the drawings are not necessarily to scale. Moreover, in the drawings, like reference numerals designate corresponding parts throughout the several views.

DETAILED DESCRIPTION

Systems and methods for monitoring gas turbine engines are provided. In this regard, several exemplary embodiments will be described. In some embodiments, an oil analysis system receives information from various devices, such as one or more debris capture devices and one or more oil debris monitors. Notably, some embodiments can incorporate only one oil debris monitor that is configured to detect the presence of magnetic and nonmagnetic particles in the lubrication oil system of a gas turbine engine. Additionally, the debris capture devices, e.g., magnetic chip detectors, can be located at various locations of the lubrication oil system, thereby assisting in localizing the source of any debris. Information from the debris capture devices and oil debris monitor is analyzed to determine whether or not the engine is operating within predetermined limits. In some embodiments, depending upon the severity of a sensed out-of-limit condition, a notification can be provided to the cockpit of an aircraft to which the gas turbine engine is mounted. Additionally or alternatively, notification can be sent to a ground site, such as to ground maintenance personnel via wireless communication, for example.

Figure 1:
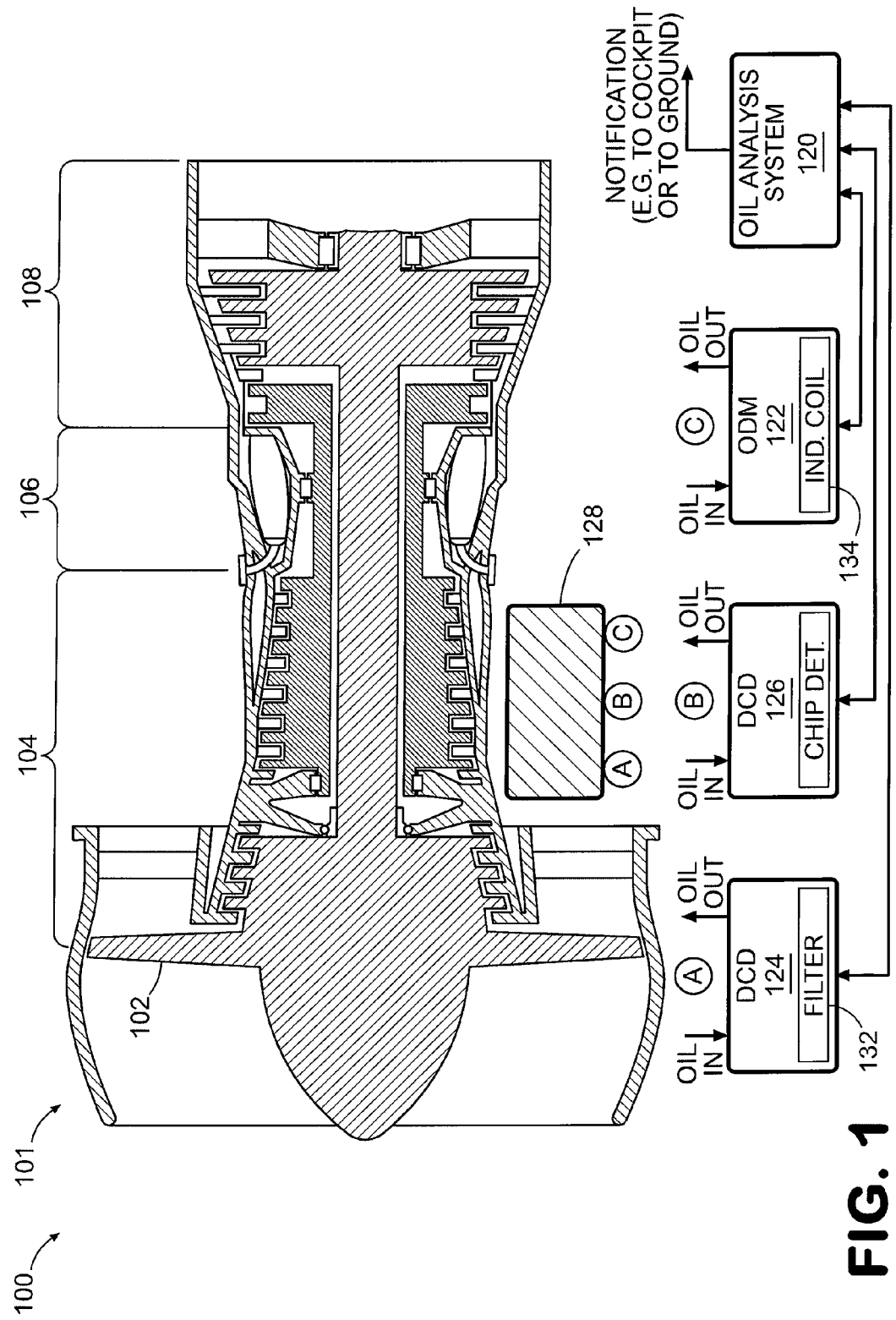
FIG. 1 is a schematic diagram of an embodiment of a system for monitoring a gas turbine engine.

Reference now made to FIG. 1, which schematically depicts an embodiment of a system for monitoring a gas turbine engine. As shown in FIG. 1, system 100 includes a gas turbine engine 101 that incorporates a fan 102, a compressor section 104, a combustion section 106 and a turbine section 108. Although engine 101 is configured as a turbofan, there is no intention to limit the invention to use with turbofans as use with other types of gas turbine engines is contemplated.

System 100 also incorporates an oil analysis system 120 that communicates with at least one oil debris monitor (ODM) and at least one debris capture device (DCD) that monitor a lubrication oil system (not shown) of the engine. In this embodiment, one ODM (122) and two DCDs (124, 126) are depicted, although various other numbers could be used in other embodiments. Notably, the DCDs and ODM are associated with an accessory gearbox 128, with DCD 124 being located at position A, DCD 126 being located at position B, and ODM 122 being located at position C.

In FIG. 1, DCD 124 incorporates a filter 132 that enables the detection of both magnetic and nonmagnetic particles carried by lubrication oil of the engine. In contrast, DCD 126 is configured as a magnetic chip detector and, thus, is only capable of detecting magnetic particles. Typically, each of the DCDs is associated with and is located downstream in the lubrication oil system of a component of the gas turbine engine that is subject to wear. Therefore, detection of debris by one of the DCDs can indicate that the associated component is degrading.

In the embodiment of FIG. 1, information regarding the presence of debris is provided to the oil analysis system 120 by the DCDs. In contrast, information corresponding to one or more characteristics of the debris is provided to the oil analysis system by ODM 122. It should be noted that, in some embodiments, the ODM can merely provided information regarding the presence of debris.

In the embodiment of FIG. 1, ODM 122 incorporates an inductor coil 134 that enables the ODM to determine one or more of debris particle size, debris particle count, debris particle mass, and debris particle composition (e.g., ferrous/non-ferrous). Each of these characteristics can be analyzed at a single point in time, cumulatively over time and/or as a rate change over time, for example.

The oil analysis system 120 correlates the information provided by the DCDs and ODM. This correlation can be used to determine: an identity of one or more components that are responsible for the debris; the extent of degradation of the one or more components; and/or whether or not the engine is operating within predetermined limits. In this regard, the oil analysis system can store data related to performance parameters of various components across a life cycle of the components. Thus, if debris is sensed and a determination is made that a particular component is the likely source of origin of the debris, one or more of the determined characteristics of the debris can be correlated with the stored performance parameters of that component. Such a correlation can be used to determine expected performance of that component. By way of example, a determination could be made that the component is operating properly, that the component requires maintenance at the next regular maintenance cycle, or that the component is approaching failure.

Regardless of the particular determination, a notification can be sent. In this regard, in some embodiments, a notification is sent to the cockpit informing the aircrew of the detected condition. Additionally or alternatively, information can be provided to ground personnel, such as via a wired or wireless interface. In the case of wireless transmission, some embodiments could transmit information corresponding to the detected condition prior to engine shutdown, such as during flight.

Figure 2:
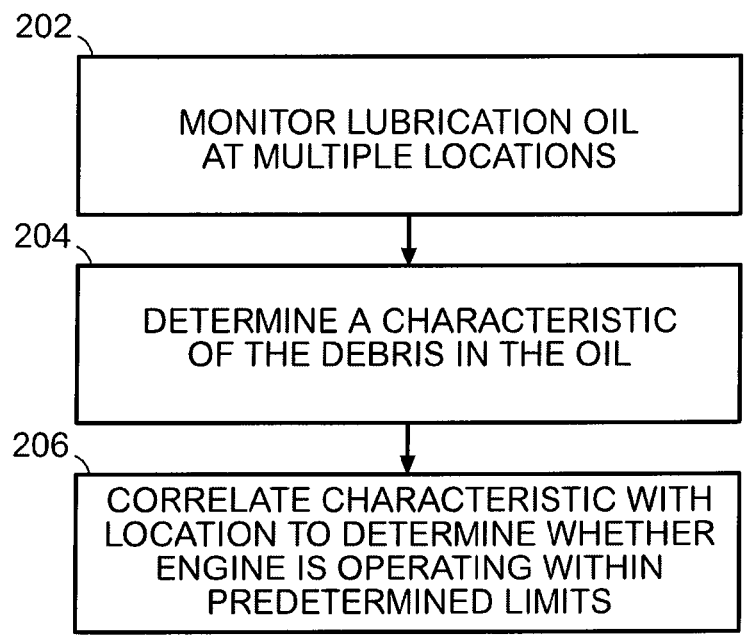
FIG. 2 is a flowchart depicting functionality of an embodiment of a system for monitoring a gas turbine engine.

FIG. 2 is a flowchart depicting functionality of an embodiment of a system for monitoring a gas turbine engine. In this regard, the functionality (or method) may be construed as beginning a block 202, in which lubrication oil is monitored at multiple locations of a gas turbine to detect a presence of debris in the oil. In block 204, a characteristic of the debris in the oil is determined. Thereafter, such as depicted in block 206, the characteristic of the debris is correlated with the location of detection to determine whether the engine is operating within predetermined limits while the gas turbine engine is operating.

Figure 3:
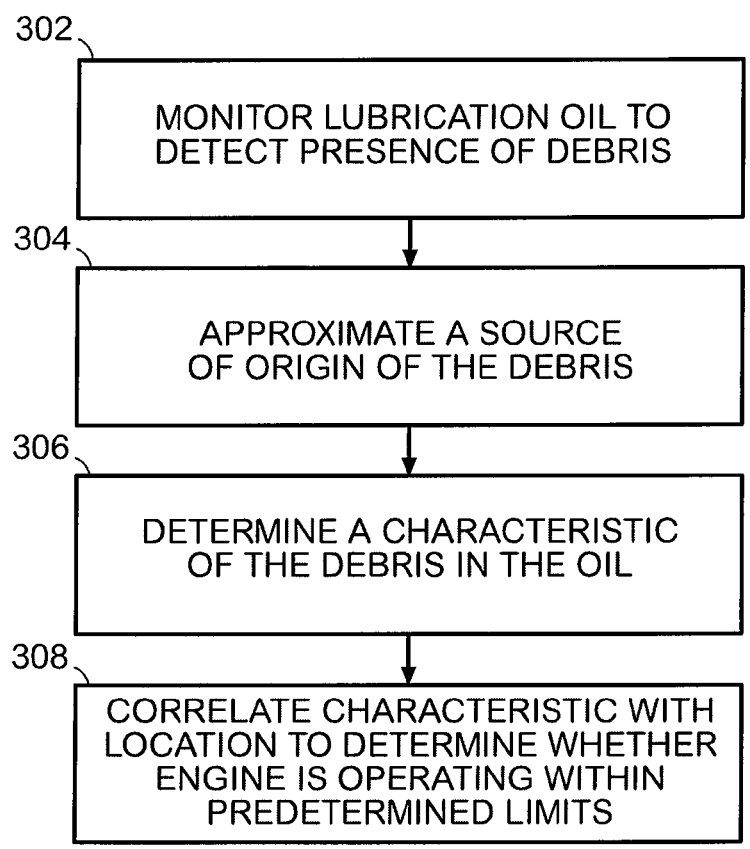
FIG. 3 is a flowchart depicting functionality of another embodiment of a system for monitoring a gas turbine engine.

FIG. 3 is a flowchart depicting functionality of another embodiment of a system for monitoring a gas turbine engine. As shown in FIG. 3, the functionality (or method) may be construed as beginning at block 302, in which lubrication oil is monitored to detect the presence of debris in the oil. In this regard, the lubrication oil can be monitored at multiple locations, such as by using a separate DCD at each such location. In block 304, a source of origin of the debris is approximated. By way of example, a first of the DCDs to detect debris can be assumed to be the closest DCD downstream of the component that is providing the debris to the lubrication oil flow. As such, once such a DCD has been identified, components upstream of that DCD can be considered suspect. Clearly, various other techniques could be used in such a determination, such as those that reference secondary indications, e.g., vibration and/or temperature indications.

In block 306, a characteristic of the debris is determined. By way of example, one or more of various characteristics, such as particle size, particle count and particle mass, can be determined by an ODM. Notably, various components have known degradation schedules over their life cycles that can, within a reasonable degree of certainty, be used to ascertain the remaining performance potential of a component based on the characteristics of debris detected.

In block 308, the characteristic of the debris is correlated with the source of the debris to determine whether the engine is operating within predetermined limits. By way of example, if the particle size of the debris exceeds a threshold particle size for a particular component, an embodiment of an oil analysis system may determine that the engine is not operating within predetermined limits. Responsive to such a determination, and depending on the degree by which the threshold value is exceeded, an alert notification may be provided. Notably, such an alert can include informing the flight crew of the detected condition and/or notifying ground maintenance personnel.

Figure 4:
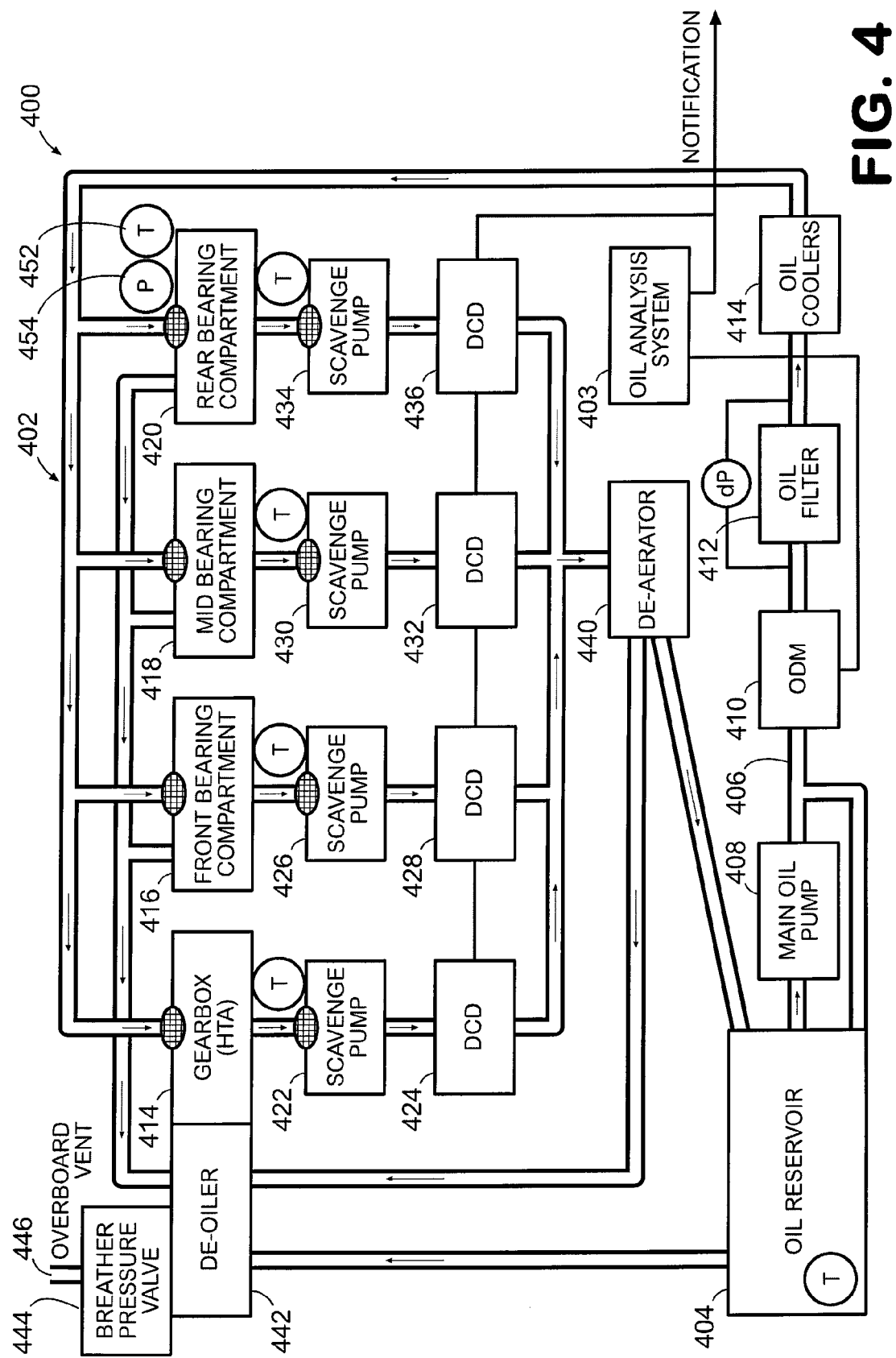
FIG. 4 is a schematic diagram of another embodiment of a system for monitoring a gas turbine engine.

Another embodiment of a system for monitoring a gas turbine engine is depicted schematically in FIG. 4. As shown in FIG. 4, system 400 includes a lubrication oil system 402 and an oil analysis system 403. The lubrication oil system generally includes an oil reservoir 404 that provides lubrication oil to conduit 406 via a main oil pump 408. From the main oil pump, the oil passes through an oil debris monitor 410 and then through a main oil filter 412 before being directed through oil cooler 414. Downstream of the oil cooler, the lubrication oil is provided to various components such as a gear box 414, as well as components associated with a front bearing compartment 416, a mid bearing compartment 418, and a rear bearing compartment 420.

Downstream of the gear box and bearing compartments are located scavenge pumps, each of which provides oil to a DCD. Specifically, scavenge pump 422 provides oil to a DCD 424, scavenge pump 426 provides oil to DCD 428, scavenge pump 430 provides oil to DCD 432, and scavenge pump 434 provides oil to DCD 436. From the DCDs, oil is provided to a de-aerator 440 that separates air from the oil. From the de-aerator, air is provided to a de-oiler 442 and then overboard via a breather pressure valve 444 and overboard vent 446. Air also is provided to the de-oiler from the gearbox and the bearing compartments, as well as from the oil reservoir in this embodiment. From the deaerator, oil is provided back to the oil reservoir.

It should also be noted that the lubrication oil system incorporates various sensors for monitoring temperature, e.g., sensor 452, and pressure, e.g., sensor 454, at multiple locations throughout the system. Although, in some embodiments, these sensors are used as inputs for operating various components, such as oil pumps and/or coolers, these sensors can be used for providing inputs to the oil analysis system for evaluating operating parameters for the gas turbine engine.

In this regard, the oil analysis system 403 can receive inputs from one or more of the DCDs as well as from the ODM. In particular, the DCDs can provide information corresponding to whether debris has been sensed in the lubrication oil. This information can be provided upon detection and/or responsive to a request for information from the oil analysis system and/or ODM 410. Notably, the ODM can provide information regarding debris to the oil analysis system in one or more of various manners. That is, the ODM can provide information corresponding to the presence of debris and/or characteristics of the debris, such as particle size, particle mass and/or particle count.

By way of example, if DCD 432 provides information to the oil analysis system indicating that debris is present in the lubrication oil, some embodiments of the oil analysis system may determine that a thrust bearing lubricated by oil of the mid bearing compartment 418 is the source of the debris. This could clearly be the case in those embodiments in which the mid-bearing compartment provides lubrication oil to only the thrust bearing and none of the other DCDs have detected debris in their respective oil flows. The oil analysis system could respond to such an indication by monitoring information provided by the ODM. In this regard, the ODM could be configured to provide information regarding particle size of the debris initially sensed by the DCD. Responsive to such information from the ODM, the oil analysis system can correlate the received information with information corresponding to thrust bearing trends in order to predict future operating parameters of the thrust bearing. If it is determined that the thrust bearing is operating within the pre-determined limits established for normal operation, a notification may or may not be sent to the flight crew. If, however, the information indicates that continued operation of the engine could result in failure of the thrust bearing and/or performance that is degraded beyond the pre-determined operating limits, notification could be sent to the flight crew so that appropriate corrective action can be taken. Regardless of whether the flight crew is notified, information corresponding to the detected debris can be stored and/or provided for later analysis, such as by ground personnel.

Various functionality, such as that described above in the flowcharts with respect to an oil analysis system, can be implemented in hardware and/or software. In this regard, a computing device can be used to implement various functionality, such as that depicted in FIGS. 2 and 3.

In terms of hardware architecture, such a computing device can include a processor, memory, and one or more input and/or output (I/O) device interface(s) that are communicatively coupled via a local interface. The local interface can include, for example but not limited to, one or more buses and/or other wired or wireless connections. The local interface may have additional elements, which are omitted for simplicity, such as controllers, buffers (caches), drivers, repeaters, and receivers to enable communications. Further, the local interface may include address, control, and/or data connections to enable appropriate communications among the aforementioned components.

The processor may be a hardware device for executing software, particularly software stored in memory. The processor can be a custom made or commercially available processor, a central processing unit (CPU), an auxiliary processor among several processors associated with the computing device, a semiconductor based microprocessor (in the form of a microchip or chip set), a macroprocessor, or generally any device for executing software instructions.

The memory can include any one or combination of volatile memory elements (e.g., random access memory (RAM, such as DRAM, SRAM, SDRAM, VRAM, etc.)) and/or non-volatile memory elements (e.g., ROM, hard drive, tape, CD-ROM, etc.). Moreover, the memory may incorporate electronic, magnetic, optical, and/or other types of storage media. Note that the memory can also have a distributed architecture, where various components are situated remotely from one another, but can be accessed by the processor.

The software in the memory may include one or more separate programs, each of which includes an ordered listing of executable instructions for implementing logical functions. A system component embodied as software may also be construed as a source program, executable program (object code), script, or any other entity comprising a set of instructions to be performed. When constructed as a source program, the program is translated via a compiler, assembler, interpreter, or the like, which may or may not be included within the memory.

The Input/Output devices that may be coupled to system I/O Interface(s) may include input devices, for example but not limited to, a keyboard, mouse, scanner, microphone, camera, proximity device, etc. Further, the Input/Output devices may also include output devices, for example but not limited to, a printer, display, etc. Finally, the Input/Output devices may further include devices that communicate both as inputs and outputs, for instance but not limited to, a modulator/demodulator (modem; for accessing another device, system, or network), a radio frequency (RF) or other transceiver, a telephonic interface, a bridge, a router, etc.

When the computing device is in operation, the processor can be configured to execute software stored within the memory, to communicate data to and from the memory, and to generally control operations of the computing device pursuant to the software. Software in memory, in whole or in part, is read by the processor, perhaps buffered within the processor, and then executed.

One should note that the flowcharts included herein show the architecture, functionality, and operation of a possible implementation of software. In this regard, each block can be interpreted to represent a module, segment, or portion of code, which comprises one or more executable instructions for implementing the specified logical function(s). It should also be noted that in some alternative implementations, the functions noted in the blocks may occur out of the order and/or not at all. For example, two blocks shown in succession may in fact be executed substantially concurrently or the blocks may sometimes be executed in the reverse order, depending upon the functionality involved.

One should note that any of the functionality described herein can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" contains, stores, communicates, propagates and/or transports the program for use by or in connection with the instruction execution system, apparatus, or device. The computer readable medium can be, for example but not limited to, an electronic, magnetic, optical, electromagnetic, infrared, or semiconductor system, apparatus, or device. More specific examples (a nonexhaustive list) of a computer-readable medium include a portable computer diskette (magnetic), a random access memory (RAM) (electronic), a read-only memory (ROM) (electronic), an erasable programmable read-only memory (EPROM or Flash memory) (electronic), and a portable compact disc read-only memory (CDROM) (optical).

It should be emphasized that the above-described embodiments are merely possible examples of implementations set forth for a clear understanding of the principles of this disclosure. Many variations and modifications may be made to the above-described embodiments without departing substantially from the spirit and principles of the disclosure. All such modifications and variations are intended to be included herein within the scope of this disclosure and protected by the accompanying claims.

The invention claimed is:

1. A method for monitoring a gas turbine engine comprising:
   monitoring lubrication oil, at multiple locations of the gas turbine engine, to detect a presence of debris in the oil;
   approximating a source of origin of the debris;
   determining a characteristic of the debris; and
   correlating the characteristic with the source to determine whether the engine is operating within predetermined limits;
   the monitoring, approximating, determining and correlating being performed while the gas turbine engine is operating.

2. The method of claim 1, wherein, in monitoring the lubrication oil, at least one of the locations is monitored by an oil debris monitor that comprises an induction coil.

3. The method of claim 2, wherein, in monitoring the lubrication oil, at least one of the locations, other than the location monitored by the oil debris monitor, is monitored by a debris capture device.

4. The method of claim 3, wherein the debris capture device is a magnetic chip detector.

5. The method of claim 3, wherein the debris capture device comprises a filter that is operative to detect magnetic and non-magnetic debris.

6. The method of claim 1, wherein:
   in monitoring the lubrication oil, multiple oil monitoring components are monitored; and
   approximating a source of origin comprises determining which of the oil monitoring components first detected the debris.

7. The method of claim 6, wherein:
   each of the oil monitoring components is associated with a corresponding engine component; and
   approximating a source of origin further comprises attributing the debris to the engine component associated with the oil monitoring component that detected the debris.

8. The method of claim 1, wherein at least one of the predetermined limits is a debris limit.

9. The method of claim 1, further comprising providing an alert indication responsive to determining that the engine is not operating within at least one of the predetermined limits.

10. The method of claim 1, further comprising providing multiple debris detection devices fluidly connected to an oil debris monitor, wherein the lubrication oil is monitored at each of the multiple locations with a respective one of the debris detection devices, and wherein the characteristic of the debris is determined by the oil debris monitor.

11. The method of claim 10, wherein the multiple debris detection devices comprise multiple debris capture devices.

* * * * *